United States Patent [19]

Wolf et al.

[11] Patent Number: 5,229,484
[45] Date of Patent: Jul. 20, 1993

[54] N-SUBSTITUTED POLYAMIDE-IMIDE

[75] Inventors: Peter Wolf, Frankenthal; Juergen Koch, Neuhofen, both of Fed. Rep. of Germany

[73] Assignee: BASF Aktiengesellschaft, Ludwigshafen, Fed. Rep. of Germany

[21] Appl. No.: 822,261

[22] Filed: Jan. 17, 1992

[30] Foreign Application Priority Data

Jan. 18, 1991 [DE] Fed. Rep. of Germany ....... 4101379

[51] Int. Cl.$^5$ .............................................. C08G 73/14
[52] U.S. Cl. ..................................... 528/322; 528/28; 528/41; 528/327; 528/331; 548/461; 548/462
[58] Field of Search ............... 528/322, 327, 331, 353, 528/28, 41

[56] References Cited

U.S. PATENT DOCUMENTS 3,179,635   4/1965   Frost et al. .......................... 528/184
4,847,353   7/1989   Watanabe ............................ 528/184

Primary Examiner—Harold D. Anderson
Attorney, Agent, or Firm—Keil & Weinkauf

[57] ABSTRACT

An N-substituted polyamide-imide essentially composed of identical or different repeating units of the formula I

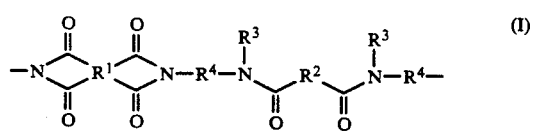

where $R^1$ is one of the following tetravalent aromatic radicals

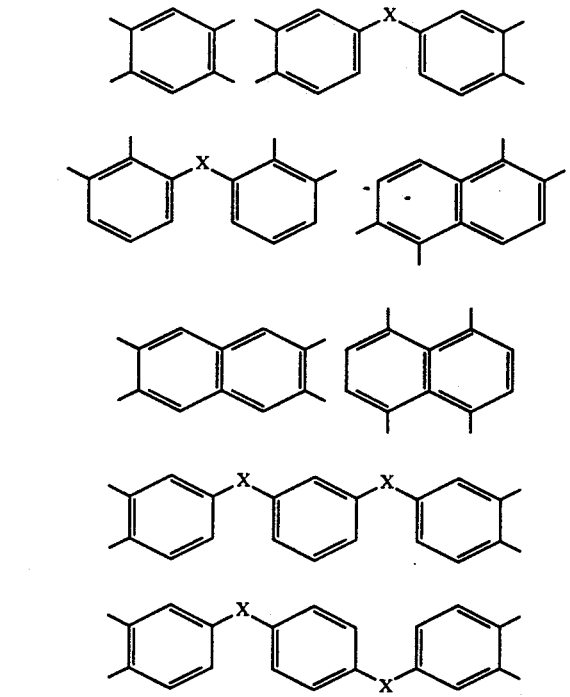

and X is a bond or one of the following linkers

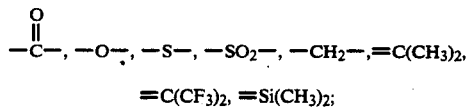

where $R^2$ and $R^4$ are each, independently of one another, one of the following divalent aromatic radicals

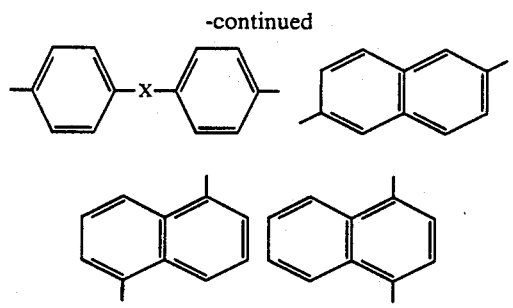
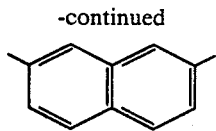
and where X has the abovementioned meanings and where $R^3$ is hydrogen or a monovalent radical such as $C_1$–$C_6$-alkyl or phenyl, and the $C_1$–$C_6$-alkyl-, $C_1$–$C_6$-alkoxy-, aryl- or halogen-substituted derivatives thereof, and precursors (monomers) therefor, are described.
5 Claims, No Drawings

N-SUBSTITUTED POLYAMIDE-IMIDE

The present invention relates to polyamide-imides which are fusible and soluble in organic solvents and which have very good heat resistance and a high glass transition temperature, and to a process for the preparation thereof.

Aromatic polyamide-imides generally have very good thermal and chemical stability. For this reason they are used in sectors requiring high stability to heat, such as in electronics or in aircraft. Polyamide-imides are used in this connection as adhesives, molded components, fibers, films, composites etc.

The disadvantage of the known polyamide-imides is the production of water during their synthesis and processing, which derives from imidization and chain-extension reactions and from a high moisture-uptake capacity. Furthermore, the solubility of the polyamide-imides in many organic solvents is very low so that it is often impossible to process such polyamide-imides from solutions.

It is an object of the present invention to provide novel plastics which are resistant to high temperatures and have the abovementioned advantages but release the minimum amount of water under the conditions of synthesis and processing and are more soluble than conventional polyamide-imides in organic solvents.

We have found that this object is achieved by novel polymers with units in the chain both of the imide type and of the N-substituted amide type, especially when the monomer units are already completely in the imide form when used. This means that the production of water which has hitherto been observed owing to imidization reactions does not occur in the preparation of the polyamide-imides according to the invention.

Surprisingly, the solubility of the polyamide-imides according to the invention is often considerably better than that of previously disclosed polyamide-imides.

The present invention directly relates to soluble and/or fusible polyamide-imides which are substituted on the amide nitrogen and have a glass transition temperature above 150° C. and, where appropriate, a melting point of up to 450° C., which are essentially composed of repeating units of the formula I

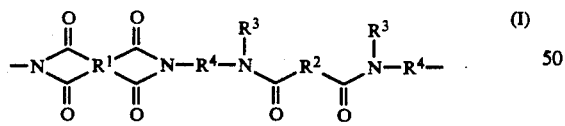

where $R^1$ is one of the following tetravalent aromatic radicals

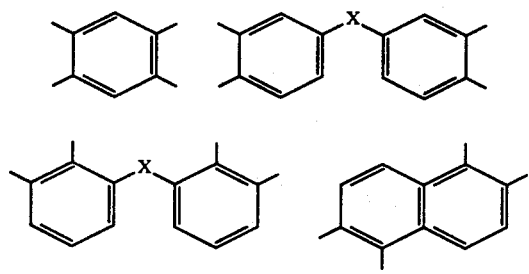

or the substitution products thereof, and X is a bond or one of the following linkers

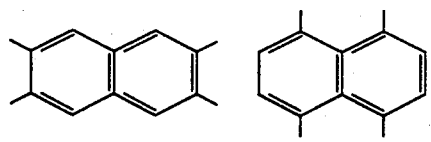

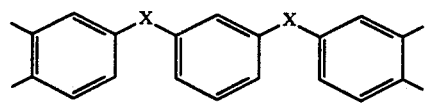

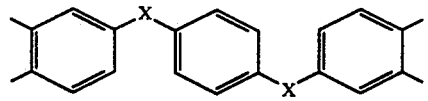

In formula (I) above, $R^2$ and $R^4$ are each, independently of one another, one of the following divalent aromatic radicals

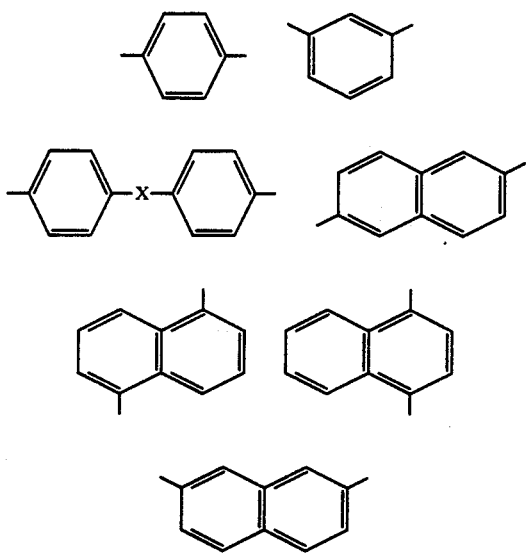

where X has the abovementioned meanings.

Finally, $R^3$ in the formula (I) above is a monovalent radical such as $C_1$–$C_6$-alkyl or phenyl or the $C_1$–$C_6$-alkyl-, $C_1$–$C_6$-alkoxy-, aryl- or halogen-substituted derivatives thereof. A certain proportion of $R^3$ radicals, for example up to 50%, may be hydrogen.

The novel polymers are advantageously obtained by polycondensation of an appropriate bis(phthalimide) of the structure (II) with an appropriate dicarbonyl halide

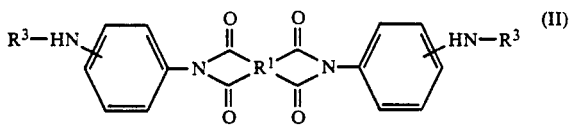

The units (monomers) of the structure (II), which have been disclosed, can be obtained, for example, by reacting N-monosubstituted phenylenediamines of the structure

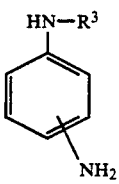

with tetracarboxylic dianhydrides in a conventional manner.

Examples of monomers (II) are

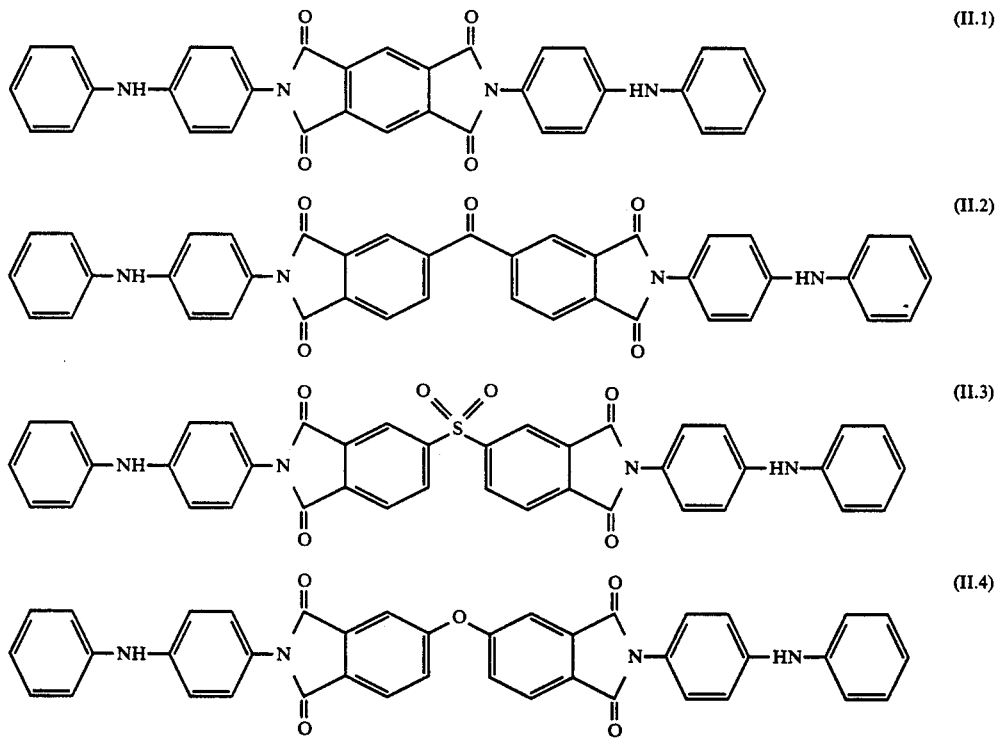

When monomers (II) in this process are partly replaced by primary diamines of the structure $H_2N$—$R$—$NH_2$ where R is any divalent organic radical it is also possible to prepare copolyamide-imides which have alkyl or phenyl on only some of the amide nitrogens (i.e. in which some of the $R^3$ radicals are hydrogen).

An alternative synthesis of the polyamide-imides (I) is the reaction of N-monosubstituted phenylenediamines with a tetracarboxylic dianhydride and subsequent reaction of the resulting intermediate with a dicarbonyl dichloride. The synthesis can in this way be carried out as a one-pot process.

The polycondensation is carried out in polar aprotic solvents which have a boiling point above 100° C., preferably above 150° C. Examples of solvents which can be used are N,N-dimethylacetamide (DMA), N-methylpyrrolidone (NMP), N-methylcaprolactam, dimethyl sulfoxide (DMSO), sulfolane, diphenyl sulfone, nitrobenzene, anisole or diphenyl ether. The reaction is carried out at form 120° C. to 300° C. depending on the reactants and the solvent.

The solids content of the solutions is generally from 10 to 50%. The reaction time depends on the required degree of condensation and on the reactivity of the monomers and is generally from 2 to 12 hours. Following the polycondensation it is possible for any free amino end groups which are present to be reacted with a monofunctional acylating agent such as benzoyl chloride for stabilization.

The reaction is generally carried out under an inert gas such as nitrogen or argon.

The reaction can be carried out in the presence of a tertiary amine such as pyridine, quinoline, isoquinoline or tri-tert-butylamine.

Preparation of the bis(phthalimide) monomers (II.1) to (II.4)

The monomers are obtained in a conventional manner, e.g. by reacting one mole equivalent of the relevant tetracarboxylic dianhydride with two mole equivalents of 4-aminodiphenylamine.

Preparation of the N-substituted polyamide-imides (I)

EXAMPLE 1

Polycondensation of the bis(phthalimide) II.2 with isophthaloyl chloride 32.73 g (50 mmol) of the bis(phthalimide) II.2 are mixed with 130 g of diphenyl sulfone and 10.15 g (50 mmol) of isophthaloyl chloride. The solid mixture is heated under nitrogen to 140° C., when the diphenyl sulfone melts. The mixture is stirred at this temperature for one hour and then heated to 170° C. and stirred for another hour. The mixture is finally heated to 200° C. and stirred for four hours. The viscous mixture is poured onto a metal plate, the solid which forms is crushed and the diphenyl sulfone is removed by extraction with hot methanol. 38.6 g (98.3%) of polymer of structure I.1 are obtained as a yellowish solid with a viscosity number of 53 ml/g (measured in NMP). The polymer has a glass transition temperature of 243° C. and is soluble in methylene chloride, chloroform, DMA and NMP and insoluble in acetone.

EXAMPLE 3

Polycondensation of the bis(phthalimide) II.3 with isophthaloyl chloride 34.54 g (50 mmol) of the bis(phthalimide) II.3 are suspended in 150 ml of NMP and then 10.15 g (50 mmol) of isophthaloyl chloride are added. The mixture is heated under nitrogen to 140° C., when a clear solution gradually forms. The mixture is stirred at this temperature for one hour and then at 170° C. for one hour.

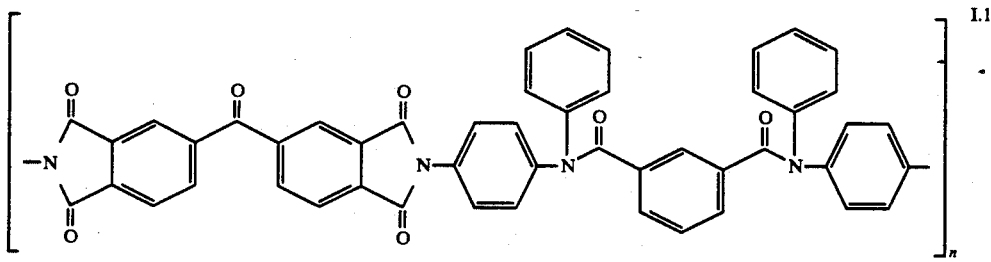

EXAMPLE 2

Polycondensation of the bis(phthalimide) II.2 with terephthaloyl chloride 32.73 g (50 mmol) of the bis(phthalimide) II.2 are mixed with 130 g of diphenyl sulfone and 10.15 g (50 mmol) of terephthaloyl chloride. The solid mixture is heated to 140° C. under nitrogen, when the diphenyl sulfone melts. The mixture is stirred at this temperature for one hour, at 170° C. for one hour and finally at 200° C. for four hours. After cooling, the solid which has formed is crushed and the diphenyl sulfone is removed by extraction with hot methanol. 38.2 g (97.3%) of polymer of structure I.2 are obtained as a yellowish solid with a viscosity number of 42 ml/g (measured in m-cresol). The polymer has a glass transition temperature of 246° C. and a melting point of 388° C.

Finally, the mixture is heated to 200° C. and stirred for four hours. The resulting product is precipitated in 600 ml of methanol, and the yellowish solid which has formed i filtered off with suction, washed thoroughly with methanol and dried under reduced pressure at 150° C. 40.6 g (98.9%) of polymer of structure I.3 are obtained as a yellowish solid with a viscosity number of 51 ml/g. The polymer has a glass transition temperature of 247° C.

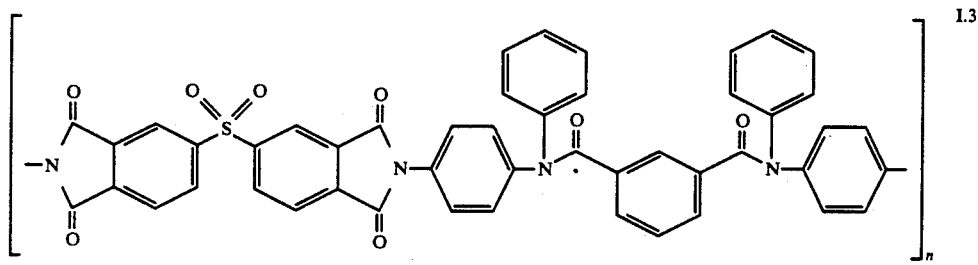

EXAMPLE 4

Polycondensation of the bis(phthalimide) II.3 with terephthaloyl chloride 34.54 g (50 mmol) of the bis(phthalimide) II.3 are suspended in 150 g of NMP and then 10.15 g (50 mmol) of terephthaloyl chloride are added. The mixture is heated under nitrogen to 140° C., when a clear solution gradually forms. The mixture is stirred at this temperature for one hour and then at 170° C. for one hour. Finally, the mixture is heated to 200° C. and stirred for

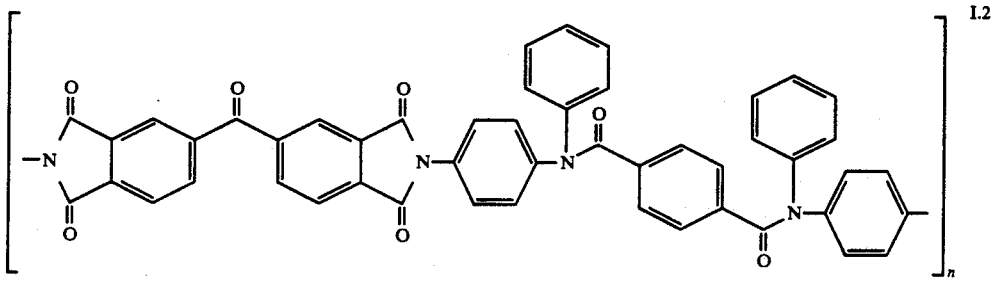

four hours. The resulting product is precipitated in 600 ml of methanol, and the yellowish solid which has formed is filtered off with suction, washed thoroughly with methanol and dried under reduced pressure at 150° C. 40.6 g (98.9%) of polymer of structure I.4 are obtained as a yellowish solid with a viscosity number of 62 ml/g. The polymer has a glass transition temperature of 230° C.

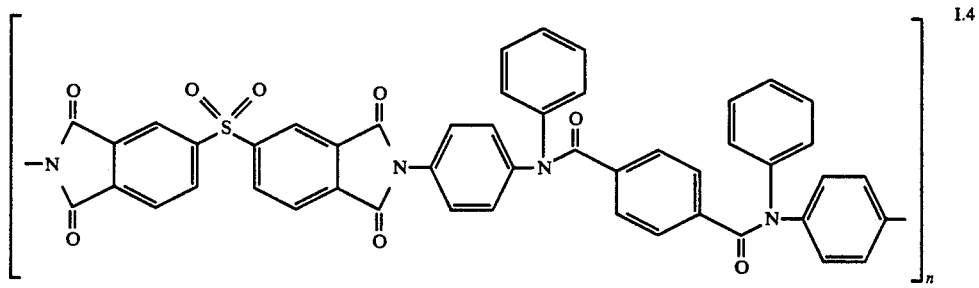

EXAMPLE 5

Polycondensation of 4-aminodiphenylamine with 5,5'-sulfonyldiphthalic dianhydride and isophthaloyl chloride (one-pot process)

22.1 g (120 mmol) of 4-aminodiphenylamine are dissolved in 200 ml of NMP under nitrogen. The mixture is cooled to 0° to 5° C. in an ice bath and then 21.49 g (60 mmol) of 5,5'-sulfonyldiphthalic dianhydride are added. The solution is stirred while cooling for 20 minutes and then the ice bath is removed and the mixture is stirred at room temperature for a further 40 minutes. 40 ml of toluene and 10 ml of isoquinoline are then added and the mixture is heated at 140°-145° C. with a water trap until no further water is collected. Then 12.18 g (60 mmol) of isophthaloyl chloride are added and the mixture is stirred for a further hour. The mixture is then distilled to remove toluene and until the temperature in the flask starts to rise above 170° C. The mixture is then stirred at this temperature for one hour and finally at 200° C. for a further four hours. The mixture is then allowed to cool and the product is precipitated in 600 ml of methanol. The resulting solid is washed with methanol and dried at 150° C. under reduced pressure. 40.3 g (98.2%) of polymer of structure I.3 are obtained as a yellowish solid with a viscosity number of 49 ml/g.

EXAMPLE 6

Polycondensation of the bis(phthalimide) II.1 with isophthaloyl chloride

The reaction is carried out as described in Example 3. The resulting polyamide-imide has a viscosity number of 43 ml/g and a glass transition temperature of 251° C.

EXAMPLE 7

Polycondensation of the bis(phthalimide) II.1 with terephthaloyl chloride

The reaction is carried out as described in Example 3. The resulting polyamide-imide has a viscosity number of 46 ml/g, a glass transition temperature of 262° C. and a melting point of 489° C.

EXAMPLE 8

Polycondensation of the bis(phthalimide) II.4 with isophthaloyl chloride

The reaction is carried out as described in Example 3. The resulting polyamide-imide has a viscosity number of 59 ml/g and a glass transition temperature of 237° C.

We claim:

1. An N-substituted polyamide-imide essentially composed of identical or different repeating units of the formula I

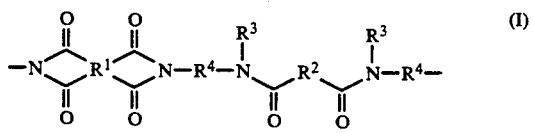

where $R^1$ is one of the following tetravalent aromatic radicals

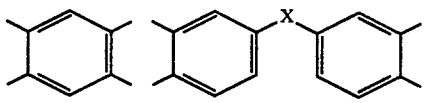

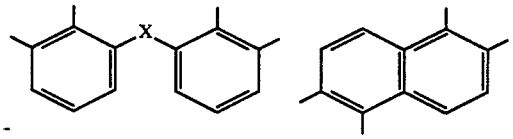

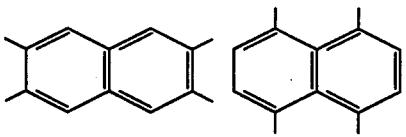

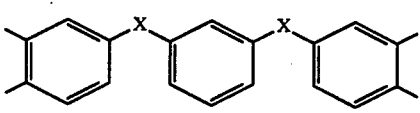

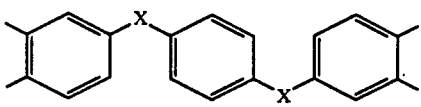

and X is a bond or X is one of the following divalent radicals

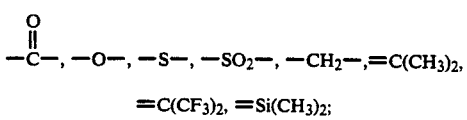

where $R^2$ and $R^4$ are each, independently of one another, one of the following divalent aromatic radicals

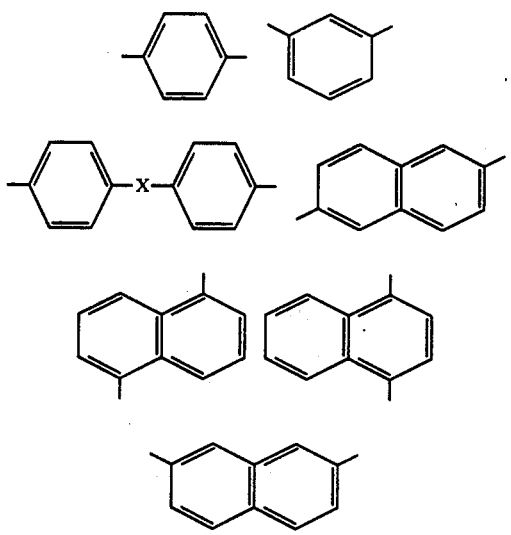

where X is defined above and where $R^3$ is hydrogen, $C_1$-$C_6$-alkyl or phenyl, and the $C_1$-$C_6$-alkyl, $C_1$-$C_6$-alkoxy, aryl- or halogen-substituted derivatives thereof, with the proviso that at least 50% of $R^3$ radicals are other than hydrogen.

2. A polyamide-imide as defined in claim 1, where $R^2$, $R^3$ and $R^4$ are phenylene, phenyl and p-phenylene respectively.

3. A partially N-substituted polyamide-imide (I) as defined in claim 1 containing repeating units of the formula

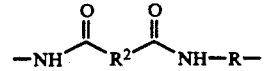

in an amount up to 90 mol %, where R is any divalent organic radical.

4. A process for preparing a polyamide-imide, as defined in claim 1, which comprises polycondensing a corresponding bis(phthalimide) with a corresponding dicarbonyl dichloride in a polar aprotic solvent at for 120° to 300° C.

5. A process for preparing a polyamide-imide as defined in claim 1, which comprises a one-pot process in which a 4-aminophenylalkylamine or a 4-aminophenylarylamine is reacted with an appropriate tetracarboxylic dianhydride in a polar aprotic solvent, and polycondensing the resulting intermediate bis(phthalimide) with an appropriate dicarbonyl dichloride at from 120° to 300° C.

* * * * *